United States Patent [19]

Violante et al.

[11] Patent Number: 4,783,484

[45] Date of Patent: Nov. 8, 1988

[54] PARTICULATE COMPOSITION AND USE THEREOF AS ANTIMICROBIAL AGENT

[75] Inventors: Michael R. Violante, Rochester; Roy T. Steigbigel, Miller Pl., both of N.Y.

[73] Assignee: University of Rochester, Rochester, N.Y.

[21] Appl. No.: 658,153

[22] Filed: Oct. 5, 1984

[51] Int. Cl.⁴ .............................................. A61K 31/24
[52] U.S. Cl. ..................................... 514/535; 514/858
[58] Field of Search ................... 514/535, 858; 424/5, 424/51

[56] References Cited

U.S. PATENT DOCUMENTS

| | | | |
|---|---|---|---|
| 2,776,241 | 1/1957 | Priewe | 260/463 |
| 2,861,024 | 11/1958 | Silver | 424/16 |
| 2,919,181 | 12/1959 | Reinhardt | 536/38 |
| 3,489,686 | 1/1970 | Parran | 252/106 |
| 3,580,853 | 5/1971 | Parran | 252/152 |
| 3,663,685 | 5/1972 | Evans | 424/1.1 |
| 3,723,325 | 3/1973 | Parran | 252/106 |
| 3,753,916 | 8/1973 | Parran | 252/107 |
| 3,761,417 | 9/1973 | Parran | 252/106 |
| 3,761,418 | 9/1973 | Parran | 252/106 |
| 3,875,071 | 4/1975 | Grand | 252/106 |
| 3,892,800 | 7/1975 | Nickel et al. | 260/518 A |
| 3,919,190 | 11/1975 | Barker et al. | 260/210 AB |
| 3,957,741 | 5/1976 | Rembaum et al. | 526/312 |
| 4,005,188 | 1/1977 | Tilly et al. | 424/5 |
| 4,009,232 | 2/1977 | Skiiki et al. | 264/9 |
| 4,059,624 | 11/1977 | Harrison | 260/565 |
| 4,105,598 | 8/1978 | Yen et al. | 521/53 |
| 4,180,619 | 12/1979 | Makhlouf et al. | 526/202 |
| 4,234,600 | 11/1980 | Sirrenberg et al. | 514/535 |
| 4,395,391 | 7/1983 | Pfeiffer | 424/5 |
| 4,406,878 | 9/1983 | DeBoer | 424/5 |

FOREIGN PATENT DOCUMENTS

867650  5/1961  United Kingdom .

OTHER PUBLICATIONS

Klebanoff, "Iodination with bacteria: a bacterial mechanism", J. Exp. Med. 126: 1063-78 (1967).
Klebanoff, "Myeloperoxidase-halide-hydrogen peroxide antibacterial System," J. Bacteriol., 95:2131 (1968).
Woeber et al., "Stimulation by phagocytosis of the deiodination of L-thyroxine in human leukocytes," Science, 176:1039 (1972).
Steigbigel et al., "Phagocytic and bactericidal properties of normal human monocytes" J. Clin. Invest., 53:131 (1974).
DeChatelet et al., "Effect of phorbol myristate acetate on the oxidative metabolism of human polymorphonuclear leukocytes," Blood, 47:545 (1976).
Violante et al., "Particulate contrast media," Invest. Radiol, 15:S329 (1980).
Violante et al., "Biodistribution of a particulate hepatolienographic CT contrast agent: A study of iodipamide ethyl ester in the rat," Invest. Radiol., 16:40 (1981).
Lauteala et al. "Effect of intraveously administered iodipamide ethyl ester particles on rat liver morphology," Inv. Radiol. 19:133 (Mar.-Apr. 1984).
Violante et al., "Protein Binding to Iothalamate Ethyl Ester," Inv. Radiol. 14:177 (1979).
Violante et al., "Maximizing hepatic contrast enhancement with a particulate contrast agent in computed tomography." (Excerpta Medica 1981).
Violante and Fischer, "Particulate Suspensions as Contrast Media," ch. 13 in Handbook of Experimental Pharmacology, vol. 73, Sovak, ed. (Springer Berlin 1984).
Grimes et al., "Formulation and Evolution of Ethiodized Oil Emulsion for Intravenous Hepatography," J. Pharmaceut. Sci. 68:52 (1979).
Fischer, "Improvement in radiographic contrast media through the development of colloidal or particulate media: An analysis," J. Theor. Biol. 67: 653-670 (1977).
Violante et al., "Particulate contrast media for computed tomographic scanning of the liver," Inv. Radiol. 15: S171 (1980).
Pullman, Violante, and Steigbigel, "Enhancement of Phagocyte Intracellular (ic) Killing by Iodipamide Ethyl Ester", Abstract, ASM Meeting, Oct. 8, 1984.
Violante et al. "Protein Binding to Iothalamate Ethyl Ester" Inv. Radiol. 14:177 (1979).
Klebanoff, J. Bacteriol, 95:2131, 1968.
Woeber et al Science, 176:1039, 1972.
Steigbigel et al., J. Clin. Invest., 53:131, 1974.
Dechatelet et al., Blood, 47:545, 1976.
Violante et al., Invest Radiol., 15: S329. 1980.
Violante et al., Invest Radiol., 16:40, 1981.

Primary Examiner—J. R. Brown
Assistant Examiner—John W. Rollins, Jr.
Attorney, Agent, or Firm—Kenyon & Kenyon

[57] ABSTRACT

A pharmaceutical composition combines a physiologically acceptable carrier with substantially uniformly sized particles of an organoiodide or organobromide which is solid at physiological tempertures, has a solubility in blood serum of less that one part per ten thousand, and has a mean particle diameter of from about 0.01 microns to about 4 microns. The method of the invention involves administering to a patient an effective amount of such particles.

29 Claims, No Drawings

PARTICULATE COMPOSITION AND USE THEREOF AS ANTIMICROBIAL AGENT

BACKGROUND OF THE INVENTION

This invention relates to particulate antimicrobial agents capable of killing intracellular microorganisms, and to the administration of these agents to patients in an effective manner.

Advances in medicinal chemistry have primarily been accomplished by the synthesis of new compounds which demonstrated improved efficacy and/or reduced toxicity because of their chemical structure. While these types of innovations continue unabated, a major objective of pharmaceutical research today involves the targetting of drugs to specific organs or tissues to maximize efficacy and minimize adverse side effects.

Despite the availability of a variety of antimicrobials, many infections continue to cause significant morbidity and mortality among patients. Several reasons can be cited to explain this phenomenon. All antimicrobials, including those exhibiting so-called broad-spectrum activity, are only effective against a finite number of organisms. In addition, bacteria are capable of developing resistance to an antibiotic by acquisition of plasmids or chromosomal mutation. These changes in the bacteria may allow for alteration of the antimicrobial agent by enzyme production or block antimicrobial agent transport into the bacteria. In addition, a bacterial strain can develop an alternative metabolic pathway or different peptide linkage and become totally resistant to a particular antibiotic. Prophylactic use of antibiotics is now generally avoided to reduce the incidence of strain specific resistance of many common bacteria.

Most organisms are susceptible to killing by the phagocytic cells. However, some microbes, so called facultative and obligate intracellular parasites, are incompletely killed by these cells. No totally effective treatment for infections by these organisms is commercially available today.

Currently administered drugs are almost exclusively water-soluble compounds with demonstrated efficacy for a particular disease or condition. Aqueous solubility of a drug permits rapid and uniform mixing with blood for delivery to the infection site; however, this phenomenon also results in drug delivery to other organs where deleterious side effects can and often do occur. In addition, high aqueous solubility often prevents a drug from entering cells which inherently limits effective treatment for numerous maladies. Surmounting these problems is a major challenge to pharmaceutical manufacturers today. Many approaches are currently being investigated and may be viable in the future. This invention, the use of particulate pharmaceuticals as antimicrobial agents, is a novel approach which shows promise for imminent clinical application.

SUMMARY OF THE INVENTION

The invention is a pharmaceutical composition and method for treating microbial infections which involves the use of particulate pharmaceuticals. The composition of the invention combines a physiologically acceptable carrier with substantially spherical, substantially uniformly sized particles of an organoiodide or organobromide which is solid at physiological temperatures, has a solubility in blood serum of less than one part per ten thousand, and has a mean particle diameter of from about 0.01 microns to about 4 microns.

The method of the invention involves administering to a patient an effective amount of the particles just described.

The preferred embodiments of the invention are: those compositions and methods as described, where the particles are capable of enhancing the intracellular killing of microorganisms; where the iodide or bromide group can be cleaved through an intracellular metabolic pathway to produce a corresponding iodine or bromine anion; where the particles are comprised of an aromatic or arylalkyl mono-, di-, or tri-iodide or bromide, iodipamide ethyl ester, iosefamate ethyl ester, or iothalamate ethyl ether; where the particles have a mean diameter of from about 1 micron to about 2 microns; where the particles have a mean diameter of from about 0.01 microns to about 0.1 microns; the composition as described, where the carrier is an aqueous solution capable of forming a suspension with the particles; the method as described, where the dose range is from about 0.003 mg to about 200 mg equivalent of iodide or bromide per kilogram body weight, or from about 0.005 mg to about 400 mg iodipamide ethyl ester per kilogram body weight respectively; the method as described where the particles are administered as an aqueous suspension; the method as described where the route of administration is parenteral; the method as described where the infection is caused by a facultative or obligate intracellular microorganisms, where the infection is caused by yeast, fungus, bacteria, mycobacteria, protozoa, chlamydia, rickettsia, helminthes or a virus; the method as described, where the target cells of the patient are phagocytes, or are the phagocytic cells of the circulatory system, liver, spleen, lungs, bone marrow, central nervous system, integument, or gastrointestinal tract; where the target cells of the patient are polymorphonuclear leukocytes, or mononuclear phagocytes.

The use of the particulate composition of the invention as an antimicrobial agent offers several advantages over available water-soluble drugs. Since water-soluble drugs are generally not transported across cell membranes, they are ineffective against intracellular parasites. It has been found in contrast that the particulate composition of the invention is phagocytosed by the same cells occupied by these parasites; therefore, the particulate composition can facilitate killing of these microbes. Furthermore, since the particulate composition is directed almost exclusively to host phagocytes which are responsible for combatting the infectious microbes, adverse side effects resulting from drug distribution to other tissues are minimized.

A technology has been developed for producing the particles used in the composition of the invention at the desired size and shape, eliminating the necessity for mechanical milling, filtering, etc. Shelf-stability of the composition has been demonstrated to be greater than six months with no indications of deterioration. When properly formulated, these compositions are stable against adverse interactions with blood components.

DETAILED DESCRIPTION OF THE INVENTION

The compounds used in the particulate composition of the invention are organoiodides and organobromides which are solid materials at physiological temperatures, and have a solubility in serum of less than one part per ten thousand, and in addition, have the foregoing properties which render it effective against microbial infections.

The use of a solid organoiodide or organobromide as a composition having antimicrobial properties according to the invention necessitates the preparation of particles of the organoidode or organobromide with a substantially uniform size. Typically, however, until the present-invention, particle suspensions with an appropriate mean diameter usually would contain a significant percentage of particles having diameters which can and will embolize small blood vessels. Also, particles of sufficiently small diameter often would, upon contact with blood, interact adversely with proteins and/or other elements of blood, interfering with normal physiological functions or producing aggregates which can embolize capillaries or other small blood vessels. Furthermore, the chemical structure of the compound forming the particles must be such that the body can metabolize and excrete it; otherwise it will remain indefinitely which could cause long-term adverse side effects. These difficulties have prevented the therapeutic use of particulate compositions until the development of this invention.

The largest useful size is determined by the fact that the particles must be capable of passing through the smallest capillaries, which are about 4 to about 5 microns in diameter, and the smallest useful size is determined by the fact that the toxicity of the particulate compositions increases as particle size decreases. Particle size must be in the range of 0.01 microns to 4 microns to be effective. Particles with a preferred size of about 1 micron demonstrate a strong antimicrobial effect, possibly because phagocytosis by certain target cells is optimal for 1 micron particles. Particles with a preferred size of about 0.01 microns to 0.1 microns are optimal for uptake by fixed macrophages of the lung and bone marrow.

The mechanisms allowing for the survival of organisms within a host phagocyte include: (a) failure of the phagocyte to mount an adequate oxidative burst; (b) lack of phagosome-lysosome fusion; (c) escape of the organism from the phagosome. The absence of an effective concentration of halide anions also plays a role. Optimal oxidative killing is dependent on the generation of highly reactive products of oxygen reduction, such as $O_2^-$ and $H_2O_2$, reacting in concert with myeloperoxidase (MPO). This reaction is further amplified by addition of a halide cofactor such as chloride or iodide. The most potent of the four biologically active halides is iodide, followed in order by bromide, chloride, and fluoride (Klebanoff; *J. Bacteriol.*, 95: 2131 (1968)). The availability of iodide to the phagocytic cell in vivo is low while the physiologic intracellular chloride concentration is in excess of the concentration required by the cell-free myeloperoxidase-mediated microbicidal assay. Thus, chloride is probably the major cofactor in vivo. However, the thyroid hormones thyroxine ($T_4$) and triiodothyronine ($T_3$) have been successfully substituted for iodide in the cell-free MPO-mediated microbicidal assay and could contribute, to a small degree, in vivo. Deiodination of $T_4$ and $T_3$ by MPO and $H_2O_2$ is known to occur. A solid organoiodide or organobromide having a cleavable iodine or bromine group would appear to be a good source of iodide or bromide, and deiodination or debromination of these compounds probably proceeds by a similar pathway. Enhanced killing of a microbe would occur when the organoiodide or organobromide and microbe are ingested simultaneously in the same phagosome, or when separate phagosomes containing the organoiodide or organobromide and microbe fuse after ingestion.

It is believed that the particulate composition of the invention enhances the phagocyte killing mechanism as described above, and thus the microbial mortality results from an in situ oxidative sterilization. Since this proposed mechanism is not specific to one cellular component or metabolic pathway, it is believed that the composition of the invention offers true broad spectrum antimicrobial activity which would not likely be circumvented by microbial mutation. This theory of action, however, is not meant to limit the invention, but rather to explain experimental evidence described below which demonstrates the intracellular microbial killing effect of the invention.

The composition of the invention includes particulate organoiodides or organobromides, wherein the organoiodides or organobromides are known compounds or their closely related derivatives having the foregoing physiological properties. For example, compounds which would be useful in the invention include bromides and iodides of alkyl, aryl, alkenyl, alkynyl, arylalkyl, arylalkenyl, or arylalkynyl groups, and in addition, these compounds may be substituted by such organic functional groups as ethers, esters, amides, carbonates, carbonyls, acids, amines or amine salts, provided that the functional groups do not interfere with the metabolic mechanism of releasing the iodide anion or bromide anion.

Preferred compounds include compounds which can be prepared as particulate solid dispersions in water because they do not have a strong tendency toward aggregation.

It has been discovered that the particulate form of the compositions of the invention makes them efficacious as antimicrobial agents. Data from experiments involving human neutrophils and *Staphylococcus aureus* indicate that an example of the particulate composition, iodipamide ethyl ester, exerts an intracellular antimicrobial effect; and this is believed to be most likely due to provision of iodide for the oxidative killing process. Thus, the compositions of the inventions act as broad spectrum antimicrobials since it is believed that microbial mutation against this mechanism is highly unlikely and it is active against a broad range of microorganisms.

Enhancement of intracellular killing is of great importance for microbes that are incompletely killed by phagocytic cells, so called facultative and obligate intracellular parasites. In the mouse, *Listeria monocytogenes* acts as a facultative intracellular organism. This invention enhances the killing of these kinds of microorganisms.

The particulate compositions of the invention are taken up by the phagocytic cells, including polymorphonuclear leukocytes, mononuclear phagocytes (tissue-fixed macrophages), and other cells of the circulatory system, central nervous system, liver, integument, gastrointestinal tract, spleen, lung, and bone marrow. A particular cellular target may be selected by varying the particle size, dose, or composition of the particulate composition.

The method of the invention effectively delivers the compounds used in the invention to phagocytic cells, where phagocytosis results, bringing the compositions of the invention into the intracellular microenvironment, where intracellular parasitic microorganisms are then killed.

The dose range of the organoiodide or organobromide particles is easily calculated in terms of the iodine or bromine content of the selected particle. At the upper range, as much as 200 mg equivalent iodide or bromide per kilogram body weight may be administered to a patient. At the lower range, a dose of 0.003 mg equivalent iodide or bromide per kilogram body weight may be administered. A desirable effect has been measured at the preferred dose range of 0.03 mg equivalent iodide or bromide per kilogram body weight.

The invention may be applied to kill intracellular microorganisms, including facultative and obligate intracellular parasites, bacteria, mycobacteria, yeast, fungi, protozoa, chlamydia, rickettsia, helminthes, viruses, and other microorganisms which are capable of surviving in the phagocytic cells of an infected host.

The compositions of the invention may be administered by conventional routes which would be apparent to those skilled in the art, and in appropriate dosage form, such as sterile aqueous solution or suspension, phosphate buffered saline, liquid solution, water, powder, elixir and the like. The compositions may be given alone in the appropriate dosage form, or combined with other pharmaceuticals or with a suitable pharmaceutical carrier. Such carriers are well known in the art and include elixirs, excipients, starches, aliphatic alcohols, glycerols, glycols, sugar solids or liquids, polyvinylpyrrolidone, suspension agents, emulsifiers, inert pharmaceutically acceptable diluting powders and liquids, isotonic solutions, gums, gelatins, lubricants, preservatives, antioxidants and the like. The methods for preparing such combinations and dosage forms are well known in the art.

Parenteral administration is preferred, but the composition of the invention may also be administered orally, bucally, peritoneally, anally, as an aerosol, or by other routes known in the art. In general, the route of administration, dosage form and amount dosage rate will be dependent upon the patient's condition and upon the judgment and observation of his attending physician.

The following examples illustrate particular aspects of the invention but do not limit the scope of the invention as set forth in the foregoing description and in the claims.

EXAMPLE 1

Preparation of Particulate Pharmaceuticals

The first step in the preparation of a particulate composition is to form a solution of the organoiodide or organobromide in an organic solvent suitable for that compound. This can occur as the compound is synthesized as a dissolved solid, or it can be done by simply dissolving particles of the compound in the solvent of choice.

The solvent is chosen to suit the compound. For example, dimethylformamide (DMF) is a solvent for iothalamate ethyl ester (ITE) and iosefamate ethyl ester (IFE), and dimethyl-sulfoxide (DMSO) in a solvent for iodipamide ethyl ester (IEE) and ITE. Any satisfactory solvent for the compound that is miscible with water can be used.

The next step is to dilute the solution with a non-solvent that does not cause the compound to precipitate. The non-solvent causes greater dispersion of the dissolved molecules of the compound in the liquid phase. Greater dilution of the solution with non-solvent produces larger particles, and less dilution of the solution with non-solvent produces smaller particles.

The non-solvent should not precipitate the compound when it is added to the solution. Non-solvents in which the compound is slightly more soluble than in water is preferred. Lower aliphatic alcohols, such as ethanol, are effective non-solvents of IEE and ITE in DMSO. Also, proportions of non-solvent to solvent at a ratio of 2 or more can produce 1 to 3 micron sized particles (depending on other parameters); and ratios of less than 2 produce sub-micron particles, at least as applied to DMSO solutions diluted with ethanol.

To precipitate the compound from the solution in a desired particle size, an aqueous solution of a surfactant is prepared in sufficient quantity to effect complete precipitation of the compound and to stabilize the resulting suspension of particles of the compound against aggregation. The surfactant provides the stabilization against aggregation, and the water is the precipitating agent. Presence of extra surfactant is advisable to ensure stabilization so that precipitated particles suspended in liquid do not aggregate, forming particles of an improperly large size. Surfactants are chosen for their compatibility with the compound and their ability to stabilize a suspension of compound particles. For work with ITE and IEE compounds, a solution of 5% C-30 or 0.1% C-15 polyvinylpyrrolidone (PVP) in water is preferred; but 5% Pluronic F-68, 0.33% gelatin, 0.33% gelatin plus 0.6% Hetastarch, 0.33% gelatin plus 0.002% propylene glycol, and 0.33% gelatin plus 2% sucrose can be used.

To precipitate particles in the desired sizes, the aqueous solution and the organic solution are combined under controlled conditions of temperature, ratio of infusion rate to stirring rate, and the proportion of non-solvent to solvent in the dispersed solution.

The precipitation of the compound occurs exothermically, heating the organic solution and resulting suspension. The temperature of the solution and resulting suspension is controlled to achieve the particle size of precipitate that is desired. Higher solution temperatures during precipitation produce larger particles, and lower solution temperatures during precipitation produce smaller particles. Also, faster infusion rates at constant stirring rate of organic solution produce smaller particles, and slower infusion rates produce larger particles.

The effects on particle size of varying parameters during precipitation of IEE from a DMSO solution diluted with 1 part solution to 2 parts ethanol using an aqueous solution of 5% PVP at different infusion rates and temperatures are as follows:

(1) As the volume and stirring of organic compound and solution are increased, the infusion rate of aqueous surfactant solution must be increased proportionally as defined by: infusion rate (ml/min.)=23+0.14 [volume (1)×stir rate (rpm)] to produce particles of 1 micron diameter at 4° C.

(2) At a constant ratio of infusion rate to [stir rate×volume], an increase in precipitation temperature produces larger particles.

(3) At a constant ratio of temperature [stir rate×volume], particle size is inversely proportional to the rate of infusion of the aqueous surfactant solution.

Thus, higher temperatures and slower mixing rates produce larger particles, and lower temperatures and faster mixing rates produce smaller particles. Another parameter than can be varied to affect particle size is the amount of dilution of the solution before precipitation occurs.

When the precipitation is complete, extra aqueous surfactant solution can be added to stabilize the suspended particles against agglomeration. The extra solution can be added at a rapid rate, since all the compound is now precipitated in uniform sized particles. The precipitated particles are promptly separated from the organic solvents to prevent redissolving and reprecipitation of particles at undesirable sizes. Centrifuging is the preferred way to do this. Promptly after separating the particles from the organic liquid, the particles are washed or rinsed with normal saline solution to remove solvent and excess surfactant.

EXAMPLE 2

Preparation of Iodipamide Ethyl Ester Particles

Particles of iodipamide ethyl ester (IEE) with a size of about 1 micron may be prepared for administration to a patient. IEE is the water-insoluble ethyl ester of iodipamide, a water-soluble radiopaque compound used clinically for radiographic examination of the gallbladder. The synthesis of iodipamide ethyl ester is known in the art (for example, esterification by alcohol and acid or by a Schotten-Bauman reaction).

IEE is only minimally soluble in water ($10^{-5}$M) and can be precipitated easily from the dimethylsulfoxide (DMSO)/ethanol solvent mixture. However, the simple addition of water to this solution results in IEE particles with extremely rough contours; these particles vary in size from less than one micron to greater than 300 microns in diameter. Since rough contours could damage vascular endothelial cells or promote aggregation, the large particles could create pulmonary emboli, a more refined procedure for controlling particle size and shape needed to be developed.

Particle Precipitation Procedure

Physical methods, such as ball milling, grinding or sonication for modifying and controlling particle size result in preparations with a very broad range of particle diameters. These methods are commonly used to eliminate large particles (greater than 4–5 microns) which could embolize in the pulmonary capillary bed, but generally some particles of submicron size are also produced; these very small particles have been shown to be more toxic than 1-2 micron particles, possibly due to increased protein binding resulting from the much larger surface area inherent with particles of smaller diameters, or possibly because of excessive uptake by bone marrow cells.

A chemical precipitation procedure for producing particles of a given size was developed to avoid these problems. By adding an aqueous solution of polyvinylpyrrolidone, at controlled rates and temperatures to IEE dissolved in a dimethylsulfoxide/ethanol solvent, apparently spherical, amorphous particles can be produced with an extremely narrow size distribution. For a particle preparation with a mean diameter of 1 micron, the total range of particle diameters is 0.4 to 2.0 microns with 90 percent of the particles ranging in size between 0.5 and 1.5 microns.

By carefully controlling precipitation parameters, particle preparations demonstrating different mean diameters, but with a similarly small range of diameters, can be produced.

The IEE particles produced using this methodology are stable in whole blood with no apparent tendency toward aggregation. When suspended in whole blood, there is essentially no tendency for the one micron IEE particles to aggregate with themselves or with formed elements of blood. The IEE particles have smooth contours.

EXAMPLE 3

The Enhancement of Phagocyte Intracellular Killing by Iodipamide Ethyl Ester Particles Facultative intracellular pathogens are capable of surviving within the mature macrophage of the host. Three mechanisms allowing for the organism's survival have been proposed: failure of the macrophage to mount an adequate oxidative burst (Wilson, *J. Exp. Med.*, 151: 328 (1980)), lack of phagosome-lyosome fusion (Lowrie et al., *Nature*, 254: 600 (1975)), and escape of the organism from the phagosome (Kress et al., *Nature*, 257: 397 (1975)).

Optimal oxidative killing is dependent upon the generation of highly reactive products of oxygen reduction such as superoxide and hydrogen peroxide reacting in concert with peroxidase and a halide such as chloride, iodide, or bromide. Attempts have been made to enhance the killing capacity of the macrophage and other phagocytic cells. Immunologically activated macrophages are capable of an increased oxidative burst and enhanced intracellular killing. However, there is not yet evidence that such immunologic manipulation can effect a cure once a naturally acquired infection is established in the host. Another approach has been to supply increased amounts of the peroxidase to the phagocyte by binding eosinophil peroxidase to an organism (*T. gondii*) before it is ingested (Locksley et al., *J. Clin. Invest.*, 69: 1099 (1982)).

Little attention has been given to manipulation of the intracellular halide content of the host cell in attempting to enhance the intracellular killing process. Accordingly, this example presents the results of experiments which assay the efect of delivering a potent halide into a phagocyte in terms of intracellular killing of *Staphylococcus aureus*. Use of this pyogenic organism allows for precise determination of the extent of its ingestion and intracellular killing. In this example the halide, iodine, was delivered by incorporation in particles of iodipamide ethyl ester, which has a high selectivity for liver and to a lesser extent spleen. (Violante et al., *Invest. Rad.*, 16: 40 (1981)). Data are presented suggesting it also has a high affinity for the neutrophil polymorphonuclear leukocyte, the most numerous circulating phagocytic cell in the body. Concomitant polymorphonuclear leukocyte ingestion of IEE particles and *S. aureus* increased the killing of the bacteria, independent of the amplitude of the respiratory burst.

(a) MATERIALS AND METHODS (i) Reagents

Trypticase soy broth (TSB) was used as the bacterial growth medium. Hanks' Balanced Salt Solution (HBSS) with 0.1% gelatin was buffered with 0.25 mM Hepes Buffer and adjusted to pH 7.2. Methylcellulose was dissolved in 2 gms/100 ml of sterile distilled water, was autoclaved and was stored at 4° C.

The particles of iodipamide ethyl ester (IEE particles) were synthesized under sterile conditions using the method described above, and were suspended in phosphate buffered saline (PBS), pH 7.3. The number of particles per suspension was determined for each newly synthesized lot in serial dilutions of PBS using a hemocytometer.

Luminol(5-amino-2,3 dihydro-1,4-phthalazinedione), was dissolved at 0.1 mM concentration in dimethyl sufoxide (DMSO) and then frozen at $-20°$ C. Zymosan was added to PBS at 50 mg/ml, boiled for 60 minutes, and frozen at $-20°$ C. Phorbol myristate acetate (PMA) was dissolved in 1 mg/ml of DMSO and 1 ml aliquots frozen at $-20°$ C. To prepare serum treated Zymosan, (STZ) Zymosan (Z) was opsonized by adding 0.4 ml of Z (50 mg/ml) to 1.6 ml autologous serum at 37° C., washed twice and adjusted to a final concentration of 10 mg/ml.

[Methyl-$^3$H]thymidine with a specific activity of 5 Ci/mM was used at a concentration of 1 mCi/ml. Lysostaphin, with a specific activity of 240 U/ml, was diluted in PBS so that 1 ml contained 10 u of activity. Trypsin was used at a concentration of 0.25%.

(ii) Preparation of leukocytes

Venous blood was first obtained from 18 normal donors who had no history of reactions to iodine containing materials, and then was heparinized (10 U/ml). The heparinized blood was diluted 20% with PBS and added to a mixture of 16 ml of PBS and 16 ml of 2% methylcellulose. After thorough mixing, the preparation was allowed to stand for 60 minutes to 23° C. The leukocyte layer was removed and contaminating RBCs removed by hypotonic lysis. The cells were then washed in PBS and the final suspension in HBSS adjusted to $10^7$PMN/ml. Differential counts of the leukocytes revealed 75% to 85% of cells were polymorphonuclear leukocytes (PMNs).

(iii) Organisms

*Staphylococcus aureus* (502A) was incubated at 37° C. in TSB for 19 hours, centrifuged at 1300 g for 20 mins, and washed in 10 ml in PBS three times. The final adjustment to the desired concentration was made by measurement of optical density at 620 mM. The actual number of organisms was determined by measuring the number of colony forming units (CFU) after the incubation period. When radiolabeled organisms were required, 60 microcuries of [methyl-$^3$H]thymidine was added to each 10 ml of TBS at the start of the 18 hour incubation.

The bacteria were opsonized with 10% autologous serum for 30 minutes at 37° C. and washed twice.

(iv) Chemiluminescence assay

Chemiluminescence of the leukocyte suspension in response to IEE particles was assayed at 37° C. A 1 ml suspension consisting of $2 \times 10^6$ PMNs/ml, and IEE particles (at 25:1 and 100:1 ratio of IEE:PMN) in HBSS was tumbled at 37° C. in 5% $CO_2$ atmosphere. At 15 and 30 minutes, 0.05 ml of the suspension was placed in an autoanalyzer cup containing 0.01 of luminol (final concentration of 0.01 mM). Chemiluminescence was measured in a scintillation counter operating in an off-coincidence mode. Each vial was recorded for 6 seconds and all vials were counted twice.

(v) Oxygen Consumption

The effect of IEE particles on STZ-stimulated oxygen consumption of PMNs was assayed using a suspension containing $5 \times 10^6$ PMN, 2 mM KCN, 1 mg STZ, IEE particles at two concentrations ($125 \times 10^6$ or $500 \times 10^6$ particles) and HBSS to bring the final volume to 2 ml. The effect of IEE particles on PMA-stimulated oxygen consumption of PMN leukocytes was assayed in the same manner with subsitution of PMA (1 microgram) for STZ. The PMNs and KCN were incubated for 10 minutes prior to the addition of the other reagents to allow for temperature equilibration. All assays were done in duplicate.

The rate of oxygen consumption by the reaction mixture was determined by the difference between the steepest rate after addition of a stimulus and the rate of the resting PMNs. The data are expressed as the percent of oxygen consumption by PMNs in the control suspension without IEE particles for each day. The lag periods were calculated from the time the reagents were added to the time determined by the intersection of the slope of oxygen consumption by the resting PMNs with the maximal slope of the stimulated PMN leukocytes.

(vi) Assay for Effect of IEE particles Upon Leukocyte Bacteriocidal and Phagocytic Capacity The effect of the IEE particles on PMN killing of *S. aureus* was performed in a standard manner. (Steigbigel et al., *J. Clin. Invest.*, 53: 131 (1974). A 1 ml suspension containing $5 \times 10^6$ PMNs, $1 \times 10^7$ opsonized *S. aureus*, IEE particles, and HBSS was tumbled in a Rotorack at 37° C. in 5% $CO_2$ with room air, and a 0.1 ml sample was removed at 30 minutes and 60 minutes. The sample was placed in 0.9 ml PBS and sonicated for 20 seconds using a Biosonik IV sonicator. The sample was then diluted and plated on TSA and the number of CFU determined at 24 hours. The results were plotted as the percentage of organisms killed in control suspensions without IEE particles at the same times.

Samples were also removed for electron microscopy and placed in 4% formaldehyde and 1% glutaraldehyde (McDowell's solution). (McDowell and Trump, Arch, Pathol. Lab. Med., 100: 405 (1976)).

Each sample was fixed in McDowell's solution for 24 hr at 4° C. The samples were washed twice in a phosphate buffer, stained with 1% solution of $OsO_4$, and washed twice with the phosphate buffer. Dehydration of the samples was accomplished by immersion in solutions of increasing ethanol concentration. After dehydration in 100% ethanol, the samples were placed in a 1:1 ratio mixture of Spurr resin and 100% ethanol and were incubated overnight at room temperature. The embedding process continued with four changes of Spurr resin within a 48 hr period. The process was completed by embedding the samples in fresh Spurr resin and heating at 60° C. for 24 hrs.

To determine the extent of phagocytosis in the presence and absence of IEE particles, 1 ml suspensions in $12 \times 75$ mm plastic tubes containing $5 \times 10^6$ PMN, $125 \times 10^6$ or $500 \times 10^6$ IEE particle, $4 \times 10^7$ opsonized radiolabeled Staphylococci (8 organisms; 1 PMN), and HBSS and were tumbled at 37° C. at 12 rpms. At 30 minutes, tubes containing leukocytes were centrifuged at 200 g for 10 minutes, decanted, and the pellet resuspended in PBS containing 10 U/ml of lysostaphin for lysis of the remaining extracellular Staphylococci. After 10 minutes in 37° C. water bath, tubes were centrifuged 10 minutes at 200 g, decanted and the pellet resuspended in 1 ml of 0.25% trypsin and placed in 37° C. water bath for 20 minutes. The tubes were then centrifuged and resuspended in 1 ml of PBS and sonicated for 20 seconds. One-half ml was pipetted into disposable glass scintillation vials and 0.1 ml diluted in 0.9 ml PBS for determination of the number of viable bacteria. In each experiment a suspension of Staphylococci without PMN, and with or without IEE particles, was centrifuged at 1100 g for 20 mins, decanted, and the pellet resuspended in 1 ml of lysostaphin as a control of lysostaphin activity, or 1 ml of PBS as a growth control.

The scintillation vials were dried at 160° C. for 2 hours, removed and cooled, and 10 ml of OCS (Organic Scintillation Fluid) was added. The counts per minute of $^3$H was determined in a liquid scintillation counter. Ingestion of *S. aureus* in the presence of IEE was calculated as the percentage of ingestion by the control PMNs without IEE particles:

$$\frac{\text{CPM/ml in the presence of } IEE \text{ particles}}{\text{CPM/ml in the absence of } IEE \text{ particles}} \times 100.$$

The number of viable intracellular organisms is expressed as:

$$\frac{\text{CFU/ml in the presence of } IEE \text{ particles}}{\text{CFU/ml in the absence of } IEE \text{ particles}} \times 100.$$

All determinations were done in duplicate.

(b) RESULTS (i) Ingestion of IEE particles by Human PMNs

Iodipamide ethyl ester particles are fairly uniform in size, averaging 1 micron in diameter and having a spherical shape. They are easily visible under the light microscope and are best distinguished in phase microscopy. They are difficult to detect in assocation with polymorphonuclear leukocytes (PMN) after a Wright's stain as they apparently blend with the granules of the PMN. However, under phase microscopy, when PMNs and particles are incubated at 37° C. in the absence of serum, significant association of the particles with the PMNs is noted.

To determine if the particles are ingested as opposed to adhering to the surface of the PMN, electron microscopy was performed on suspension of PMN and particles incubated at 37° C. for 15 and 30 mins, in the absence of serum. These studies showed particles in various phases of ingestion and enclosed within phagosomes.

(ii) Effect of IEE particles upon oxidative burst of PMNs

There was no detectable stimulation of PMN luminol-enhanced chemiluminescence at an IEE particle concentration of $125 \times 10^6$/ml or $500 \times 10^6$/ml (IEE particle: PMN ratios of 25:1 and 100:1 respectively). Nor was there evidence of an increase in oxygen consumption of PMNs when IEE particles were present at the same two concentrations. Iodipamide ethyl ester particles decreased STZ-stimulated oxygen consumption of PMNs by 18% at 25:1 IEE particle/PMN ratio ($P<0.05$) and by 33% at 100:IEE particle/PMN ($P<0.005$). Furthermore, the lag period of STZ-stimulated oxygen consumption ($1.85\pm0.3$ min without IEE particles) was increased almost two-fold at a 100:1 IEE particle/PMN ratio ($3.75\pm0.4$ min with IEE particles). At a 25:1 IEE particle:PMN ratio, no effect was noted ($1.60\pm0.013$ min).

Iodipamide ethyl ester particles also decreased oxygen consumption by the soluble stimulus, PMA, although to a lesser degree: 8% at 25:1 IEE particle/PMN ratio, ($p>0.10$), and 16% at 100:1 IEE particle:PMN ratio ($p<0.05$).

(iii) Effect of IEE particles upon PMN Phagocytosis and Bactericidal Capacity

The killing of opsonized *S. aureus* by PMNs was increased by IEE particles at a ratio of 25 IEE particles:1 PMN. There was a 34% increase in killing over that seen by PMN without IEE particle ($p<0.05$). At a higher concentration of IEE particles:PMN (100:1), there was no effect upon PMN killing of Staphylococci ($p<0.1$).

IEE particles reduce both the phagocytosis and intracellular survival of radiolabeled *S. aureus*. At 25:1 IEE particles:PMN, there is a 17% reduction in *S. aureus* ingested over control PMNs ($p<0.005$) and a 24% reduction in viable intracellular organisms ($p<0.05$) compared to control PMNs. This effect is more pronounced at a ratio of 100 IEE particles:1 PMN where a 25% decrease in ingestion was noted over controls ($p<0.005$) with a 50% decrease in viable intracellular organisms compared to the same control PMNs ($p<0.01$). Hence ingestion of IEE particles by PMN causes a reduction in phagocytosis of a second particle, in this case the Staphylococcus. However, treatment with IEE particle yields fewer intracellular viable organisms than could be accounted for on the basis of the reduction in phagocytosis alone, and thus an overall increase in the killing of Staphylococci. The assays for viable intracellular organisms and the assay of total number of Staphylococci in the suspensions both indicate that IEE particles enhance the intracellular killing of PMNs.

(c) DISCUSSION

This example demonstrates the feasibility of enhancing phagocyte intracellular microbicidal capacity by the introduction of organoiodide or organobromide particles into the cell. In this embodiment, iodide is delivered by use of iodipamide ethyl ester particles. IEE particles have a predilection for uptake by the tissue-fixed macrophages of the mononuclear phagocyte system, most notably the liver and spleen.

Incubation of [Staphylococcus aureus in a suspension of human polymorphonuclear cells resulted in phagocytosis of the bacteria but killing of only some of these organisms. The addition of iodipamide ethyl ester particles to this system, at a ratio of 25:1 IEE particles:PMN, resulted in a small decrease in the number of organisms phagocytosed, presumably due to competitive phagocytosis of IEE particles. However, the intracellular survival rate was much lower in the presence of IEE particles so that there was an overall significant net enhancement in the number of *S. aureus* killed. This enhanced kill rate is believed to result from release by IEE particles of free iodide which catalyzes the reaction producing peroxide and superoxide radicals. Since these experiments were conducted in the absence of serum, complement activation or other non-specific mechanisms can be ruled out. Also, zymosan particles, employed as controls in these experiments, did not produce the same effects as IEE particles, indicating again that IEE particles act by means of a specific, rather than a non-specific or general activation mechanism.

The interaction of the IEE particles and the most numerous circulating phagocytic cell in humans, the polymorphonuclear leukocyte (PMN), was examined in vitro. Several aspects of this interaction were of interest. First, ingestion by PMNs of the IEE particles proceeded in the absence of serum. Second, there was no oxidative burst associated with ingestion of IEE particles by the PMNs. Third, when IEE particles were incubated with PNMs and opsonized *S. aureus,* an increase in intracellular killing was observed.

Addition of serum might enhance the rate and number of those IEE particles ingested, but significant association of IEE particles with PMNs was seen in its absence and transmission EM studies confirmed the intracellular location of those particles.

The absence of an oxidative burst during phagocytosis of IEE particles by PMNs may suggest the following beliefs concerning of the potential mechanisms by which IEE particles can enhance intracellular killing.

Unopsonized IEE particles did not stimulate an oxidative burst when they were ingested. In fact, IEE particles inhibited oxygen consumption by PMNs stimulated with STZ, probably on the basis of competition for binding sites on the surface of the PMN. Inhibition of the ingestion process after binding, or inhibition of the energy-requiring activation of the oxidative burst might also be involved in the diminution of the oxidative burst noted with IEE particles. A partial contribution of the latter mechanism may be supported by the observation of a small but significant decrease in oxygen consumption of PMNs in the presence of IEE particles. PMA is a soluble stimulus and not dependent on phagocytosis (DeChatelet et al., *Blood*, 47: 545 (1976)). It is possible that a mechanism of IEE particle inhibition of STZ-oxygen consumption may be due to decreased phagocytosis of the stimulating particle, because a significantly diminished PMN uptake of radiolabeled *S. aureus* in the presence of IEE particles is observed.

Increased killing of opsonized *S. aureus* by PMNs was observed in the presence of IEE particles. Two types of assays were used to measure PMN killing of the organism. In the first, the reduction of the initial inoculum of opsonized bacteria is measured over time in the presence of PMN. This assay was performed at a bacteria:PMN ratio of 2:1 which in the absence of IEE particles allows for phagocytosis of all organisms by 30 min. At a 25:1 IEE particle:PMN ratio, significantly increased killing of the bacteria was observed despite any potential inhibition of ingestion. These experiments indicate an enhancement of intracellular killing which was substantiated in the second assay which examines only intracellular viable organisms.

For these experiments a higher ratio of bacteria:PMN (8:1) is used. In this assay improved intracellular killing was most evident at a 100:1 IEE particle:PMN ratio. This was not merely due to increased efficiency in intracellular killing due to fewer organisms ingested in the presence of IEE particle, since an increase in killing of *S. aureus* was demonstrated in the assay of total killing. Furthermore, since IEE particles were not opsonized, the possibility of enhancement of intracellular killing by complement or antibody is ruled out (Leijh et al., *J. Clin. Invest.*, 63: 772 (1979)).

It follows that the increased killing of *S. aureus* by PMNs in the presence of IEE particles is the result of ingestion of these particles, which provides an increased supply of iodide to phagolysosomes. The microbicidal capacity of the PMN which is mediated by hydrogen peroxide ($H_2O_2$) is amplified by myeloperoxidase, and is further enhanced by addition of a halide (iodide or bromide) cofactor. Since these IEE particles are known to disappear over time once taken up by the tissue-fixed macrophages (Violante et al., *Invest. Rad.*, 16: 40 (1981)), it is possible that there is transport of deorganified iodide into a phagosome containing an infectious microbe. For example, electron microscopic studies do show simultaneous ingestion of *S. aureus* and IEE particles, as well as both together within a phagosome.

Thus, iodipamide ethyl ester particles enhance the killing of microbes such as *S. aureus* by human PMNs. This enhancement of killing of *S. aureus* by PMNs may be due to increased availability of iodide or bromide to the phagosome and enhancement of the microbicidal capacity of the PMN.

EXAMPLE 4

Treatment of a Mammalian Infection with a Particulate Pharmaceutical

A particulate antimicrobial composition alone, or in combination with a water-soluble drug, provides significantly improved efficacy in combatting microbial infections caused by a wide range of intracellular organisms. The following data supports this efficacy.

(a) *Staphylococcus aureus*-In Vivo Experiments

A mouse model was employed to predict the effectiveness of clinical treatment with particulate pharmaceuticals. Specific pathogen-free Swiss-Webster derived mice (Crl: $CD^R$-1(1CR)BR) were intravenously innoculated with *Staphylococcus aureus* (ATCC No. 6538) at $1 \times 10^8$ organisms/mouse. The first group of ten mice which were maintained untreated as controls demonstrated a 20 percent survival rate ($LD_{80}$) after 10 days. A second group of ten mice were given a single intravenous injection of one micron iodipamide ethyl ester particles 90 minutes after the *S. aureus* injection. The IEE particle dose was 0.3 mg/kg iodine per kilogram body weight. The survival rate for this group at day 10 was fifty percent ($LD_{50}$), or 150 percent higher than the untreated controls. A third group, given the same dose of IDE but at 48 hours post *S. aureus* injection, had a survival rate of sixty percent ($LD_{40}$), or 200 percent greater than controls. Thus, a single, low-dose injection of IEE particles dramatically increased the survival rate of these *Staphylococcus aureus* infected mice.

(b) *Listeria monocytogenes*-in Vivo Experiments

A mouse model was employed to evaluate the in vivo efficacy of IEE particles against an intracellular facultative organism, *Listeria monocytogenes*.

Specific pathogen-free Swiss-Webster derived mice (Crl: $CD^R$-1 (1CR)BR) were intravenously innoculated with $10^3$–$10^4$ Listeria monocytogenes per mouse. Ninety minutes later the mice were intravenously injected with phosphate-buffered saline (controls) or IEE particles at 70 mg iodine per kilogram body weight (equivalent to clinical liver CT imaging dose level for humans). Mice were sacrificed (ether overdose) in groups of five each at 24 hour intervals post-Listeria injection. At the time of sacrifice, spleens were removed, homogenized in phosphate-buffered saline and plated in agar for subsequent determination of the number of viable organisms as a function of time post-Listeria innoculation.

Typical results from these experiments demonstrated no difference in Listeria survival rates between control and IEE particle-treated mice at 24 hours post innoculation. However, at both 48 and 72 hours post innoculation, the number of viable Listeria was significantly less in the mice treated with IEE particles as compared with controls. These results indicate that IEE particles enhance the kill-rate of the facultative intracellular organism, *Listeria monocytogenes* in this mouse model. Microorganisms of this type are a major cause of life-threatening infections throughout the world and, at present, treatment of these infections is inadequate. The enhancement of host defense by use of a particle of solid organoiodide or organobromide according to the invention offers promise as a highly effective method of treatment for obligate and facultative intracellular microorganisms, including bacteria, protozoa, fungi, yeast, helminthes rickettsia, chalmydia, and viruses.

We claim:

1. A pharmaceutical composition suitable for treating a microbial infection of a patient which comprises a physiologically acceptable carrier in combination with an effective amount of substantially uniformly sized particles which are essentially comprised of an organoiodide or organobromide which is solid at physiological temperatures and has a solubility in blood serum of less than one part per ten thousand, and wherein the mean particle diameter is from about 0.01 microns to about 4 microns.

2. The composition according to claim 1, wherein the particles are capable of enhancing intracellular killing of microorganisms.

3. The composition according to claim 1, wherein the iodide or bromide group can be cleaved through an intracellular metabolic pathway to produce a corresponding iodine or bromine anion.

4. The composition according to claim 1, wherein the particles are comprised of an aromatic or arylalkyl mono-, di-, or tri-iodide or bromide.

5. The composition according to claim 1, wherein the particles are comprised of iodipamide ethyl ester.

6. The composition according to claim 1, wherein the particles are comprised of iosefamate ethyl ester.

7. The composition according to claim 1, wherein the particles are comprised of iothalamate ethyl ester.

8. The composition according to claim 1, wherein the mean particle diameter is from about 1 micron to about 2 microns.

9. The composition according to claim 1, wherein the mean particle diameter is from about 0.01 microns to about 0.1 microns.

10. The composition according to claim 1, wherein the carrier is an aqueous solution capable of forming a suspension with the particles.

11. A method for treating a microbial infection which comprises administering internally to a patient with an infection caused by an intracellular microorganism an effective amount of substantially uniformly sized particles which are essentially comprised of an organoiodide or organobromide which is solid at physiological temperatures and has a solubility in blood serum of less than one part per ten thousand, and wherein the mean particle diameter is from about 0.01 microns to about 4 microns, together with a physiologically acceptable carrier.

12. The method according to claim 11, wherein microorganisms are present in target cells of the patient and the administration of the particles enhances intracellular killing of the microorganisms.

13. The method according to claim 12, wherein the target cells are phagocytes.

14. The method according to claim 12, wherein the target cells are the phagocytic cells of the circulatory system, liver, spleen, lung, bone marrow, central nervous system, integument, or gastrointestinal tract.

15. The method according to claim 12, wherein the target cells are polymorphonuclear leukocytes or mononuclear phagocytes.

16. The method according to claim 11, wherein the iodide or bromide group is cleaved through an intracellular metabolic pathway to produce a corresponding iodine or bromine anion.

17. The method according to claim 11, wherein the particles are comprised of an aromatic or arylalkyl mono-, di-, or tri-iodide or bromide.

18. The method according to claim 11, wherein the particles are comprised of iodipamide ethyl ester.

19. The method according to claim 11, wherein the particles are comprised of iodipamide ethyl ester and the dose is from about 0.005 mg to about 400 mg of iodipamide ethyl ester per kilogram body weight.

20. The method according to claim 11, wherein the particles are comprised of iosefamate ethyl ester.

21. The method according to claim 11, wherein the particles are comprised of iothalamate ethyl ester.

22. The method according to claim 11, wherein the mean particle diameter is from about 1 micron to about 2 microns.

23. The method according to claim 11 wherein the mean particle diameter is from about 0.01 microns to about 0.1 microns.

24. The method according to claim 11, wherein the particles are administered as an aqueous suspension.

25. The method according to claim 11, wherein the route of administration is parenteral.

26. The method according to claim 11, wherein the dose is that amount of particles calculated to contain from about 0.003 mg to about 200 mg equivalent of iodide or bromide per kilogram body weight.

27. The method according to claim 11, wherein the infection is caused by a facultative or obligate intracellular parasite.

28. The method according to claim 11, wherein the infection is caused by a fungus, a yeast, a bacteria, a helminthes, a rickettsia, a chlamydia, a protozoa, a mycobacteria, or a virus.

29. The method according to claim 11, wherein the particle comprises iodipamide ethyl ester of a particle size of about 1 micron to about 2 microns, and the dose is about 0.05 mg iodipamide ethyl ester per kilogram body weight.

* * * * *